United States Patent
Shaw (10) Patent No.: US 12,268,459 B2
(45) Date of Patent: Apr. 8, 2025

(54) PHYSICAL MEDICAL ELEMENT AFFIXATION SYSTEMS, METHODS, AND MATERIALS

(71) Applicant: Intuitive Surgical Operations, Inc., Sunnyvale, CA (US)

(72) Inventor: Ryan W. Shaw, San Jose, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 519 days.

(21) Appl. No.: 17/101,710

(22) Filed: Nov. 23, 2020

(65) Prior Publication Data

US 2021/0153959 A1    May 27, 2021

Related U.S. Application Data

(60) Provisional application No. 62/940,351, filed on Nov. 26, 2019.

(51) Int. Cl.
*A61B 34/35* (2016.01)
*A61B 34/00* (2016.01)
*A61B 34/20* (2016.01)

(52) U.S. Cl.
CPC .............. *A61B 34/35* (2016.02); *A61B 34/20* (2016.02); *A61B 34/76* (2016.02); *A61B 34/77* (2016.02); *A61B 2034/2065* (2016.02); *A61B 2034/2068* (2016.02)

(58) Field of Classification Search
CPC ......... A61B 34/35; A61B 34/20; A61B 34/76; A61B 34/77; A61B 2034/2065; A61B 2034/2068; A61B 90/94; A61B 2017/00119; A61B 2017/00123; A61B 2090/3937; A61B 34/37; A61B 2090/064; A61B 90/06

See application file for complete search history.

(56) References Cited

U.S. PATENT DOCUMENTS

| | | | | |
|---|---|---|---|---|
| 5,603,318 A * | 2/1997 | Heilbrun | ............... | H04N 13/239 348/E13.016 |
| 7,758,345 B1 * | 7/2010 | Christensen | ............. | A61C 9/00 433/213 |
| 7,844,320 B2 * | 11/2010 | Shahidi | .................... | A61B 5/06 600/407 |
| 7,892,247 B2 * | 2/2011 | Conston | ............... | A61B 50/362 606/155 |

(Continued)

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

*Primary Examiner* — Anh Tuan T Nguyen
*Assistant Examiner* — Shankar Raj Ghimire (57) ABSTRACT

An exemplary system is configured to access image data representative of an image of an internal space of a patient, the image depicting a physical medical element positioned over an anatomical surface within the internal space, identify a region, within the image, that depicts a fiducial marker on the physical medical element, determine, based on the identified region, an affixation target location on the physical medical element, and assist, based on the determined affixation target location, an affixation process in which the physical medical element is affixed to the anatomical surface.

20 Claims, 9 Drawing Sheets

(56) References Cited

U.S. PATENT DOCUMENTS

| | | | | |
|---|---|---|---|---|
| 9,220,570 B2 * | 12/2015 | Kim | | A61B 34/76 |
| 9,402,691 B2 * | 8/2016 | Merritt | | A61C 9/0046 |
| 9,795,446 B2 * | 10/2017 | DiMaio | | A61B 34/10 |
| 11,589,863 B2 * | 2/2023 | Weir | | A61B 17/068 |
| 2001/0010004 A1 * | 7/2001 | Traxel | | A61B 90/39 |
| | | | | 606/130 |
| 2002/0107518 A1 * | 8/2002 | Neubauer | | A61B 90/39 |
| | | | | 606/54 |
| 2002/0133236 A1 * | 9/2002 | Rousseau | | A61F 2/0063 |
| | | | | 623/23.72 |
| 2003/0083648 A1 * | 5/2003 | Wang | | A61B 34/70 |
| | | | | 606/1 |
| 2003/0158477 A1 * | 8/2003 | Panescu | | A61B 34/20 |
| | | | | 600/424 |
| 2004/0106916 A1 * | 6/2004 | Quaid | | A61B 34/71 |
| | | | | 606/1 |
| 2004/0152972 A1 * | 8/2004 | Hunter | | G16Z 99/00 |
| | | | | 128/899 |
| 2005/0113846 A1 * | 5/2005 | Carson | | A61B 90/10 |
| | | | | 606/130 |
| 2005/0228270 A1 * | 10/2005 | Lloyd | | A61B 90/36 |
| | | | | 600/407 |
| 2005/0267529 A1 * | 12/2005 | Crockett | | A61B 17/0643 |
| | | | | 606/215 |
| 2006/0098851 A1 * | 5/2006 | Shoham | | A61B 34/30 |
| | | | | 382/128 |
| 2007/0088340 A1 * | 4/2007 | Brock | | A61B 34/72 |
| | | | | 606/1 |
| 2007/0142825 A1 * | 6/2007 | Prisco | | A61B 34/70 |
| | | | | 606/1 |
| 2007/0235768 A1 * | 10/2007 | Nakazawa | | H01L 29/66212 |
| | | | | 257/E29.338 |
| 2007/0238982 A1 * | 10/2007 | Caylor, III | | A61B 5/1127 |
| | | | | 600/424 |
| 2007/0270660 A1 * | 11/2007 | Caylor, III | | A61B 34/20 |
| | | | | 600/300 |
| 2008/0125630 A1 * | 5/2008 | Caylor | | A61B 90/36 |
| | | | | 600/300 |
| 2008/0262390 A1 * | 10/2008 | Bangera | | A61B 90/39 |
| | | | | 606/1 |
| 2008/0262523 A1 * | 10/2008 | Makower | | A61F 5/0073 |
| | | | | 606/192 |
| 2009/0088897 A1 * | 4/2009 | Zhao | | A61B 34/30 |
| | | | | 700/250 |
| 2010/0161129 A1 * | 6/2010 | Costa | | B25J 9/1697 |
| | | | | 901/47 |
| 2010/0168562 A1 * | 7/2010 | Zhao | | A61B 90/94 |
| | | | | 600/426 |
| 2010/0168763 A1 * | 7/2010 | Zhao | | A61B 90/94 |
| | | | | 606/130 |
| 2011/0019884 A1 * | 1/2011 | Blau | | A61B 90/37 |
| | | | | 382/128 |
| 2011/0160570 A1 * | 6/2011 | Kariv | | A61B 6/12 |
| | | | | 600/424 |
| 2011/0288568 A1 * | 11/2011 | Capuzziello | | A61F 2/0063 |
| | | | | 606/151 |
| 2012/0071890 A1 * | 3/2012 | Taylor | | A61B 5/6817 |
| | | | | 606/129 |
| 2012/0130159 A1 * | 5/2012 | Abri | | A61B 90/50 |
| | | | | 600/102 |
| 2013/0190726 A1 * | 7/2013 | Kesner | | A61M 25/0133 |
| | | | | 604/95.01 |
| 2013/0253550 A1 * | 9/2013 | Beisel | | A61B 17/11 |
| | | | | 606/153 |
| 2014/0018824 A1 * | 1/2014 | Julian | | A61B 1/00149 |
| | | | | 606/130 |
| 2014/0178832 A1 * | 6/2014 | Choi | | A61C 1/084 |
| | | | | 433/27 |
| 2014/0229007 A1 * | 8/2014 | Kishi | | B25J 13/02 |
| | | | | 700/257 |
| 2014/0343416 A1 * | 11/2014 | Panescu | | A61B 34/30 |
| | | | | 600/431 |
| 2015/0100066 A1 * | 4/2015 | Kostrzewski | | A61B 34/30 |
| | | | | 606/130 |
| 2015/0150457 A1 * | 6/2015 | Wu | | A61B 5/445 |
| | | | | 600/425 |
| 2016/0324523 A1 * | 11/2016 | Lukin | | A61B 17/1114 |
| 2017/0079722 A1 * | 3/2017 | O'Grady | | A61G 13/04 |
| 2017/0181825 A1 * | 6/2017 | Hunter | | A61F 2/0059 |
| 2017/0210012 A1 * | 7/2017 | Larkin | | A61B 1/0005 |
| 2017/0219339 A1 * | 8/2017 | Mueller | | G01B 11/272 |
| 2017/0265866 A1 * | 9/2017 | Ryou | | A61B 17/3478 |
| 2017/0323062 A1 * | 11/2017 | Djajadiningrat | | G06F 16/3326 |
| 2018/0014888 A1 * | 1/2018 | Bonny | | A61B 34/20 |
| 2018/0070860 A1 * | 3/2018 | Gupta | | A61B 5/1079 |
| 2018/0098766 A1 * | 4/2018 | Weir | | A61B 17/0686 |
| 2018/0116731 A1 * | 5/2018 | State | | A61B 17/07207 |
| 2019/0008624 A1 * | 1/2019 | Francois | | G01B 5/00 |
| 2019/0021796 A1 * | 1/2019 | Timperley | | A61B 34/30 |
| 2019/0059696 A1 * | 2/2019 | Hirayama | | A61B 1/00009 |
| 2020/0038108 A1 * | 2/2020 | Chou | | A61B 34/10 |
| 2020/0100881 A1 * | 4/2020 | Emery, III | | A61C 8/0009 |
| 2020/0129240 A1 * | 4/2020 | Singh | | A61B 34/10 |
| 2020/0229893 A1 * | 7/2020 | Browd | | A61B 90/37 |
| 2020/0331147 A1 * | 10/2020 | Larkin | | B25J 9/1697 |
| 2021/0022693 A1 * | 1/2021 | Brewer | | A61B 6/12 |
| 2021/0196399 A1 * | 7/2021 | Ayvali | | A61B 34/20 |
| 2021/0366012 A1 * | 11/2021 | Raynor | | G06Q 30/0613 |
| 2022/0361958 A1 * | 11/2022 | Manwaring | | A61B 90/11 |
| 2023/0270504 A1 * | 8/2023 | Mozes | | A61B 34/76 |
| | | | | 606/1 |

* cited by examiner

PHYSICAL MEDICAL ELEMENT AFFIXATION SYSTEMS, METHODS, AND MATERIALS

RELATED APPLICATIONS

The present application claims priority to U.S. Provisional Patent Application No. 62/940,351, filed on Nov. 26, 2019, and entitled "PHYSICAL MEDICAL ELEMENT AFFIXATION SYSTEMS, METHODS, AND MATERIALS," the contents of which are hereby incorporated by reference in their entirety.

BACKGROUND INFORMATION

A computer-assisted surgical system is often used to perform a hernia repair procedure within a patient. As part of the hernia repair procedure, a mesh patch may be placed over the hernia and affixed (e.g., sutured) to tissue surrounding the hernia. The mesh patch may provide support for the damaged tissue as the tissue heals.

During a hernia repair procedure, a surgeon interacting with the computer-assisted surgical system must size the mesh patch (e.g., by cutting the mesh patch out of a mesh material) and place the mesh patch at an appropriate location within the patient. The surgeon must then suture the mesh patch at appropriate suture locations on the mesh patch. These operations may be time-intensive and tedious.

SUMMARY

The following description presents a simplified summary of one or more aspects of the systems and methods described herein. This summary is not an extensive overview of all contemplated aspects and is intended to neither identify key or critical elements of all aspects nor delineate the scope of any or all aspects. Its sole purpose is to present one or more aspects of the systems and methods described herein as a prelude to the detailed description that is presented below.

An exemplary system includes a memory storing instructions; and a processor communicatively coupled to the memory and configured to execute the instructions to: access image data representative of an image of an internal space of a patient, the image depicting a physical medical element positioned over an anatomical surface within the internal space; identify a region, within the image, that depicts a fiducial marker on the physical medical element; determine, based on the identified region, an affixation target location on the physical medical element; and assist, based on the determined affixation target location, an affixation process in which the physical medical element is affixed to the anatomical surface.

An exemplary method includes accessing, by a medical element management system, image data representative of an image of an internal space of a patient, the image depicting a physical medical element positioned over an anatomical surface within the internal space; identifying, by the medical element management system, a region, within the image, that depicts a fiducial marker on the physical medical element; determining, by the medical element management system, based on the identified region, an affixation target location on the physical medical element; and assisting, based on the determined affixation target location, an affixation process in which the physical medical element is affixed to the anatomical surface.

An exemplary material includes a top surface; a plurality of concentric lines printed on the top surface of the material and that define a plurality of concentric regions, the concentric lines configured to guide a user in cutting a patch out of the material for placement over an anatomical surface in an internal space of a patent; and a plurality of fiducial markers printed on the top surface within each of the concentric regions, the fiducial markers configured to be recognized within an image utilizing a machine vision heuristic while the patch is placed over the anatomical surface and guide an affixing of the patch to the anatomical surface by an affixation device coupled to a manipulator arm of a computer-implemented surgical system.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Physical medical element affixation systems, methods, and materials are described herein. As described herein, an exemplary medical element management system may access image data representative of an image of an internal space of a patient, the image depicting a physical medical element positioned over an anatomical surface within the internal space. The medical element management system may further identify a region, within the image, that depicts a fiducial marker on the physical medical element and determine, based on the identified region, an affixation target location on the physical medical element. The medical element management system may assist, based on the determined affixation target location, an affixation process in which the physical medical element is affixed to the anatomical surface.

An exemplary material may include a top surface and a plurality of concentric lines printed on the top surface of the material and that define a plurality of concentric regions. The concentric lines may be configured to guide a user in cutting a patch out of the material for placement over an anatomical surface in an internal space of a patent. The material may further include a plurality of fiducial markers printed on the top surface within each of the concentric regions. The fiducial markers may be configured to be recognized within an image utilizing a machine vision heuristic while the patch is placed over the anatomical surface and guide an affixation of the patch to the anatomical surface by an affixation device coupled to a manipulator arm of a computer-implemented surgical system. The material may further include a bottom surface configured to adhere to the anatomical surface in the internal space of the patient.

The systems, methods, and materials described herein advantageously provide guidance during an affixation (e.g., suturing, stapling, gluing, etc.) of a physical medical element over an anatomical surface within the body during a medical procedure. Such guidance may facilitate automatic affixation (e.g., suturing) of the physical medical element on the anatomical surface. Moreover, the systems and methods described herein may minimize an amount of time required to suture the physical medical element on the anatomical surface, which may be beneficial to the patient and to a surgical team involved in suturing the physical medical element on the anatomical surface. These and other advantages and benefits of the systems and methods described herein will be made apparent herein.

As used herein, a physical medical element refers to any element foreign to a patient's body that is configured to be placed on and cover an anatomical surface within the patient's body. For example, a physical medical element may be implemented by a patch (e.g., a mesh patch) configured to cover a tissue defect (e.g., a hernia, cut, or other type of lesion) within the patient. Other examples of physical medical elements that may be used in connection with the systems and methods described herein include, but are not limited to, gauze, bandages, plates, prostheses, etc. A physical medical element may be placed on an anatomical surface in any suitable manner. While the description generally refers to the physical medical element being sutured to the anatomical surface, the physical medical element may be affixed in any suitable manner (e.g., anchored, stapled, glued, etc.) to the anatomical surface using the methods and systems described herein.

Figure 1:
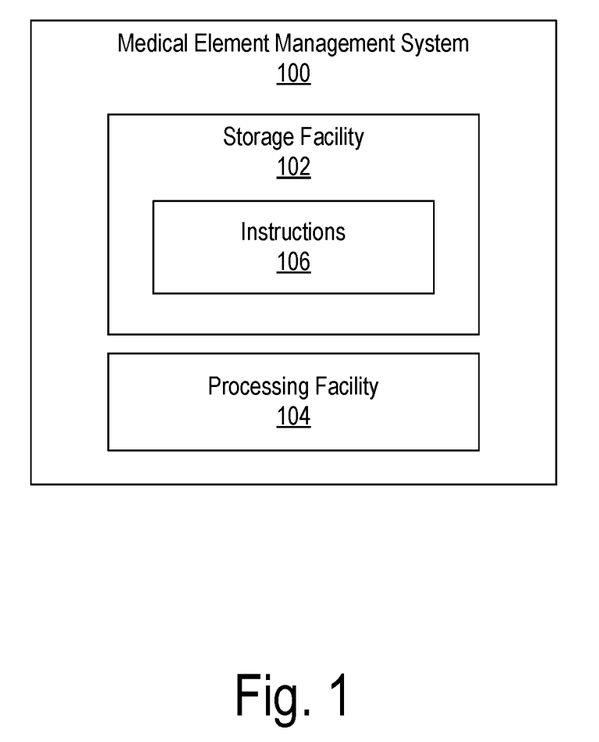
FIG. 1 illustrates an exemplary medical element management system according to principles described herein.

FIG. 1 illustrates an exemplary medical element management system 100 ("system 100") configured to perform various operations described herein. As shown, system 100 may include, without limitation, a storage facility 102 and a processing facility 104 selectively and communicatively coupled to one another. Facilities 102 and 104 may each include or be implemented by hardware and/or software components (e.g., processors, memories, communication interfaces, instructions stored in memory for execution by the processors, etc.). For example, facilities 102 and/or 104 may be implemented by any component in a computer-assisted surgical system configured to perform a medical procedure in which a physical medical element is introduced into a body of a patient and affixed (e.g., sutured) to an anatomical surface within the body of the patient. As another example, facilities 102 and/or 104 may be implemented by a computing device separate from and communicatively coupled to a computer-assisted surgical system. In some examples, facilities 102 and 104 may be distributed between multiple devices and/or multiple locations as may serve a particular implementation.

Storage facility 102 may maintain (e.g., store) executable data used by processing facility 104 to perform one or more of the operations described herein. For example, storage facility 102 may store instructions 106 that may be executed by processing facility 104 to perform one or more of the operations described herein. Instructions 106 may be implemented by any suitable application, software, code, and/or other executable data instance. Storage facility 102 may also maintain any data received, generated, managed, used, and/or transmitted by processing facility 104.

Processing facility 104 may be configured to perform (e.g., execute instructions 106 stored in storage facility 102 to perform) various operations described herein.

For example, processing facility 104 may be configured to access image data representative of an image of an internal space of a patient, the image depicting a physical medical element positioned over an anatomical surface within the internal space, identify a region, within the image, that depicts a fiducial marker on the physical medical element, determine, based on the identified region, a suture target location on the physical medical element, and direct a suturing device coupled to a manipulator arm of a computer-assisted surgical system to suture the physical medical element to the anatomical surface at the suture target location.

These and other operations that may be performed by system 100 (e.g., processing facility 104) are described herein.

Figure 2:
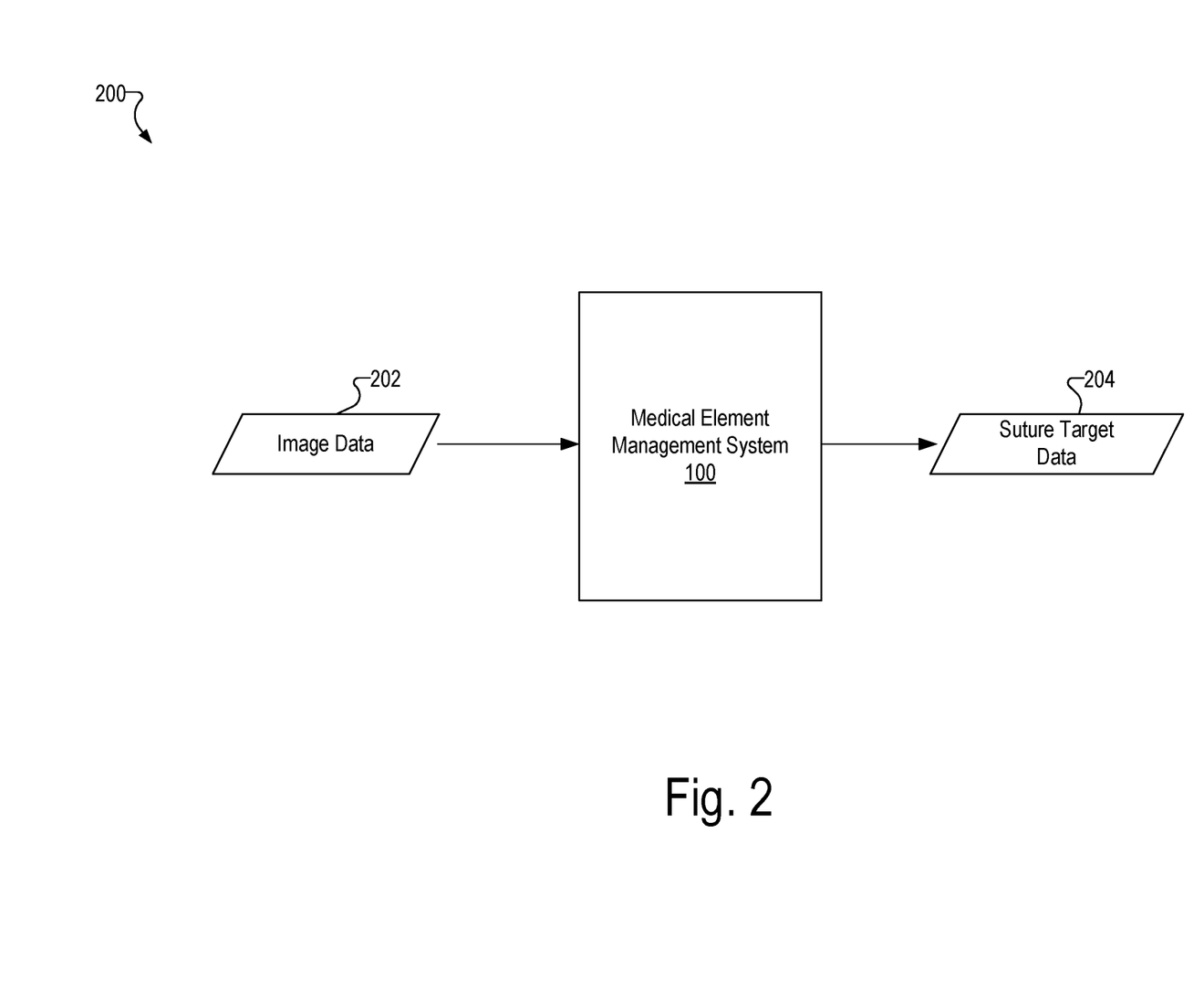
FIG. 2 illustrates an exemplary configuration of a medical element management system according to principles described herein.

FIG. 2 illustrates an exemplary configuration 200 in which system 100 is configured to identify suture target locations within an image that is acquired by an imaging device and that depicts an anatomical surface to be covered by a physical medical element. As shown, system 100 may access image data 202 representative of an image acquired by an imaging device and depicting an internal space of a patient. Based on image data 202, system 100 may identify one or more suture target locations within the image that depict locations at which a physical medical element is to be sutured to an anatomical surface. System 100 may output suture target data 204 representative of the identified suture target locations.

Image data 202 may be provided by any suitable imaging device. For instance, the imaging device may be implemented by an endoscope or other camera device configured to capture images of a scene. In some examples, the imaging device may be configured to be attached to and controlled by a computer-assisted surgical system. In alternative examples, the imaging device may be hand-held and operated manually by an operator (e.g., a surgeon).

In some examples, the scene captured by the imaging device may include a surgical area associated with a patient. The surgical area may, in certain examples, be entirely disposed within the patient and may include an area within the patient at or near where a surgical procedure is planned to be performed, is being performed, or has been performed. For example, for a minimally invasive surgical procedure being performed on tissue internal to a patient, the surgical area may include the tissue, anatomy underlying the tissue, as well as space around the tissue where, for example, surgical instruments used to perform the surgical procedure are located. In certain example implementations, the surgical area entirely disposed within the patient may be referred to as an "internal space." As described herein, any internal anatomy of the patient (e.g., vessels, organs, and/or tissue) and/or surgical instruments located in the internal space may be referred to as objects and/or structures.

Suture target data 204 may be in any suitable format. For example, suture target data 204 may include two or three-dimensional pixel coordinates representative of pixels that depict the suture target locations. Additionally or alternatively, suture target data 204 may include two or three-dimensional coordinates representative of physical locations in the internal space.

System 100 may identify suture target locations based on image data 202 in any suitable manner. For example, system 100 may use image processing and/or machine vision heuristics (e.g., algorithms, techniques, etc.) to determine target suture locations. For instance, system 100 may use edge detection heuristics to determine an edge of the physical medical element. System 100 may determine target suture locations to be at points a specified distance from the edge of the physical medical element. Additionally or alternatively, the physical medical element may include fiducial markers configured to be detected using machine vision heuristics of system 100. The machine vision heuristics may identify regions within the image that depict fiducial markers. System 100 may determine target suture locations based on the identified regions.

Figure 3:
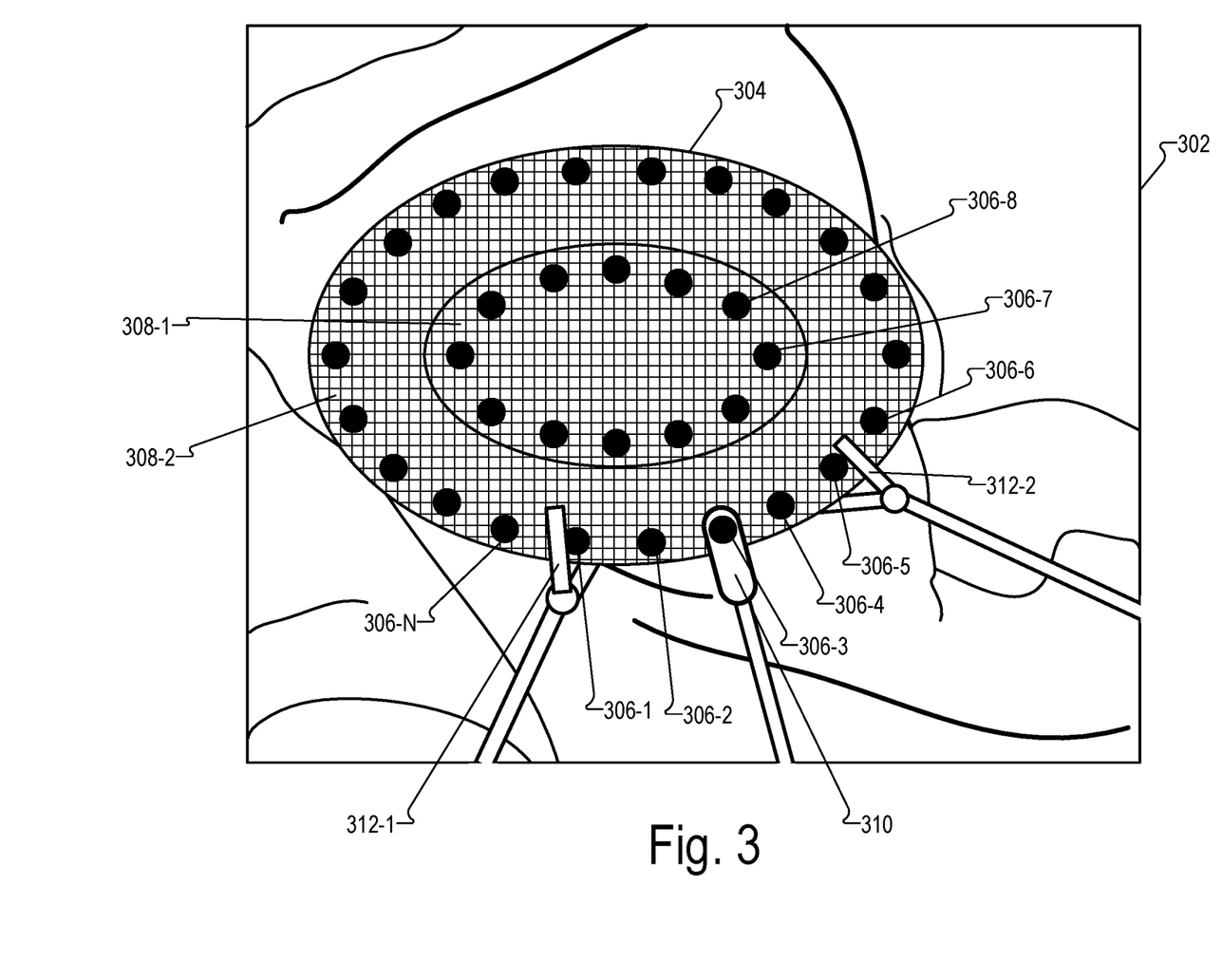
FIG. 3 shows an exemplary scenario in which a physical medical element is being placed on an anatomical surface according to principles described herein.

To illustrate, FIG. 3 shows an exemplary image 302 that may be captured by an imaging device aimed at an internal space of a patient and that may be represented by image data 202. Image 302 shows a physical medical element 304, which may be placed on a tissue defect. Physical medical element 304 includes fiducial markers 306 (e.g., fiducial marker 306-1 through 306-N), which may be configured to be detected by system 100 using machine vision heuristics. System 100 may determine target suture locations based on fiducial markers 306.

For example, system 100 may use machine vision heuristics to detect regions that depict fiducial markers 306. Additionally or alternatively, system 100 may use any suitable techniques to detect regions that depict fiducial markers 306. As shown, physical medical element 304 includes two concentric regions 308 (e.g., concentric region 308-1 and 308-2) of fiducial markers 306. While concentric regions 308 of physical medical element 304 are shown to be elliptical in shape, concentric regions 308 may be any suitable shape (e.g., circle, square, triangle, polygon, etc.) that share a center and/or a center region.

System 100 may determine an outermost concentric region (e.g., concentric region 308-2) of concentric regions depicting fiducial markers 306 and use the outermost concentric region of concentric regions to determine target suture locations. System 100 may determine the outermost concentric region in any suitable manner. For instance, system 100 may determine vectors directing outward from a center of physical medical element 304 and use a last detected region depicting a fiducial marker of fiducial markers 306 for each vector to determine the outermost concentric region for determining target suture locations. Additionally or alternatively, system 100 may use vectors passing across physical medical element 304 and use a first and last detected region depicting fiducial markers 306 to determine the outermost concentric region for determining target suture locations. In some examples, physical medical element 304 may include only one concentric region of fiducial markers 306, making the one concentric region an outermost concentric region.

The target suture locations may be determined based on outermost fiducial markers 306 in any suitable manner. For instance, based on fiducial marker 306-3, a target suture location may be on fiducial marker 306-3, or a specified distance from fiducial marker 306-3 (e.g., a centimeter or any other suitable length to a side of fiducial marker 306-3 or a length radially toward or away from a center of physical medical element 304 from fiducial marker 306-3), or in between fiducial marker 306-3 and a next fiducial marker 306-4.

System 100 may assist, based on the determined target suture locations, a suturing process in which physical medical element 304 is sutured to the anatomical surface. For example, system 100 may direct a suturing device 310 to suture physical medical element 304 to the anatomical surface at the target suture locations. Suturing device 310 may be coupled to a manipulator arm of a computer-assisted surgical system, which may be coupled to system 100 and/or include system 100. In some examples, suturing device 310 is controlled by a computer-assisted surgical system (e.g., by being connected to a manipulator arm of the computer-assisted surgical system). In these examples, suturing device 310 may be referred to as a certain type of surgical instrument coupled to and controlled by the computer-assisted surgical system. In alternative examples, suturing device 310 is not controlled by a computer-assisted surgical system. In these alternative examples, suturing device 310 may be manually held and/or otherwise controlled by a user and system 100 may provide an indication of the target suture locations to the user for suturing physical medical element 304 to the anatomical surface.

In some examples, system 100 may also direct surgical instruments 312-1 and 312-2 ("surgical instruments 312"), which may include (among other suitable instruments) any suitable grasping tool configured to hold and guide physical medical element 304 into place. Surgical instruments 312 may also be coupled to manipulator arms of the computer-assisted surgical system. In other examples, surgical instruments 312 may be controlled by user input commands provided by a surgeon or other user.

Figure 4:
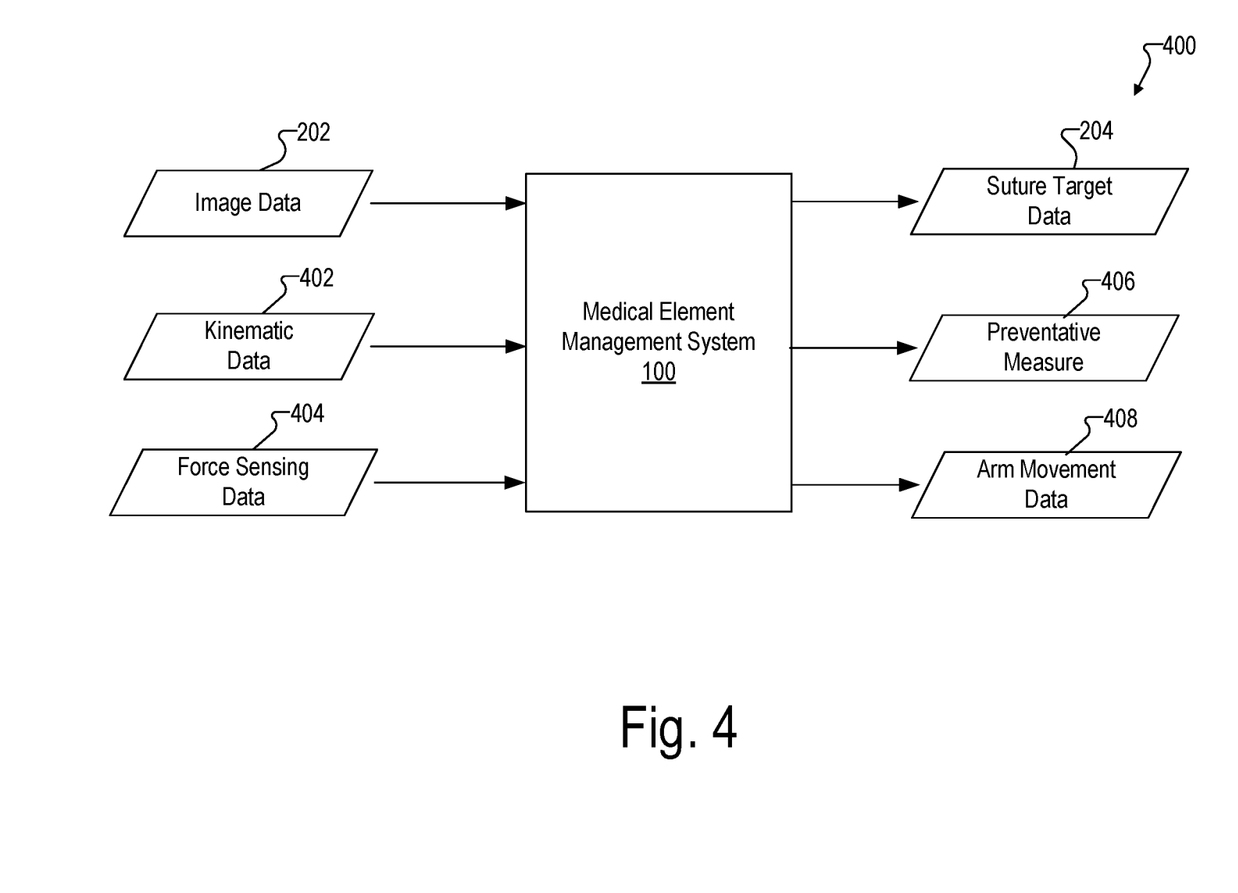
FIG. 4 illustrates another exemplary configuration of a medical element management system according to principles described herein.

For instance, FIG. 4 shows another exemplary configuration 400 of system 100. In configuration 400, system 100 receives image data 202 and also receives kinematic data 402 and force sensing data 404. System 100 uses image data 202, kinematic data 402, and/or force sensing data 404 to provide suture target data 204, a preventative measure 406, and/or arm movement data 408.

Kinematic data 402 may include kinematic information indicating a position and/or an orientation of a surgical instrument (e.g., surgical instrument 312-1 and/or surgical instrument 312-2) and/or a manipulator arm. Such information may be provided by one or more sensors (e.g., displacement transducers, orientational sensors, positional sensors, etc.) included on surgical instrument 312-1 and/or the manipulator arm configured to provide kinematic information.

Force sensing data 404 may include information indicating an amount of external force applied to a surgical instrument (e.g., surgical instrument 312-1 and/or surgical instrument 312-2) and/or the manipulator arm. Such information may be provided by one or more sensors included on surgical instrument 312-1 and/or the manipulator arm configured to output force sensing data.

In addition to suture target data 204 as described above, configuration 400 shows system 100 providing preventative measure 406 based on image data 202, kinematic data 402, and/or force sensing data 404. For example, system 100 may determine a potential collision between a suturing device (e.g., suturing device 310) and surgical instrument 312-1 based on image data 202 and/or kinematic data 402. Potential collisions may be detected in any suitable manner such as by analyzing image data 202 and/or kinematic data 402 to determine positions and/or velocities of suturing device 310 and surgical instrument 312-1. System 100 may further determine whether the positions are within a threshold amount of each other and/or the velocities may result in such positions. Based on the detection of the potential collision, system 100 may perform one or more of preventative measure 406.

Preventative measure 406 may include any suitable measure configured to prevent the potential collision. For example, preventative measure 406 may include providing a warning to a user of system 100. The warning may include any suitable alert to draw the user's attention to the potential collision, such as a visual alert (e.g., on a display of a computer-assisted surgical system), an audio alert (e.g., through a speaker of the computer-assisted surgical system), a haptic alert (e.g., through a user control system of the computer-assisted surgical system), etc. The user may respond to the warning to prevent the collision by providing a user input command to suturing device 310 and/or surgical instrument 312-1 (e.g., via manipulating arms of the computer-assisted surgical system) to move away from each other, to move in a different direction, stop a movement toward each other, etc. Additionally or alternatively, the warning may include a suggestion for such a user input command to prevent the collision and allow the user to input the command by responding to the warning.

Additionally or alternatively, preventative measure 406 may also include an automatic response provided by system 100. For instance, preventative measure 406 may include an automatic stopping of a movement of suturing device 310 and/or surgical instrument 312-1, automatic movement of suturing device 310 and/or surgical instrument 312-1 away from each other, etc. Additionally or alternatively, preventative measure 406 may include coordinating movement of suturing device 310 and/or surgical instrument 312-1 such that collisions would be avoided. Such coordinated movements may be provided as arm movement data 408.

System 100 may provide arm movement data 408 to the computer-assisted surgical system to control movement of suturing device 310 and/or surgical instruments 312. For example, arm movement data 408 may include data representative of movements to coordinate suturing device 310 and surgical instruments 312 so that suturing device 310 and surgical instruments 312 are prevented from occupying a same position and/or within a threshold distance from each other, to prevent collisions among suturing device 310 and surgical instruments 312. Additionally or alternatively, arm movement data 408 may include data representative of movements to coordinate suturing device 310 and surgical instruments 312 to automatically suture a physical medical element (e.g., physical medical element 304) to an anatomical surface at a tissue defect.

For instance, system 100 may provide arm movement data 408 to instruct suturing device 310 and surgical instruments 312 to move to positions as shown in image 302. Thus, system 100 instructs surgical instrument 312-1 to hold physical medical element 304 at fiducial marker 306-1 (or at a suture target location based on fiducial marker 306-1, a holding location based on fiducial marker 306-1, etc.), surgical instrument 312-2 to hold physical medical element 304 at fiducial marker 306-5, and suturing device 310 to suture physical medical element 304 at a suture target location based on fiducial marker 306-3. Once suturing is complete at the suture target location based on fiducial marker 306-3, system 100 may then coordinate movements of suturing device 310 and surgical instruments 312 to a next set of fiducial markers 306, such as shown in FIG. 5.

Figure 5:
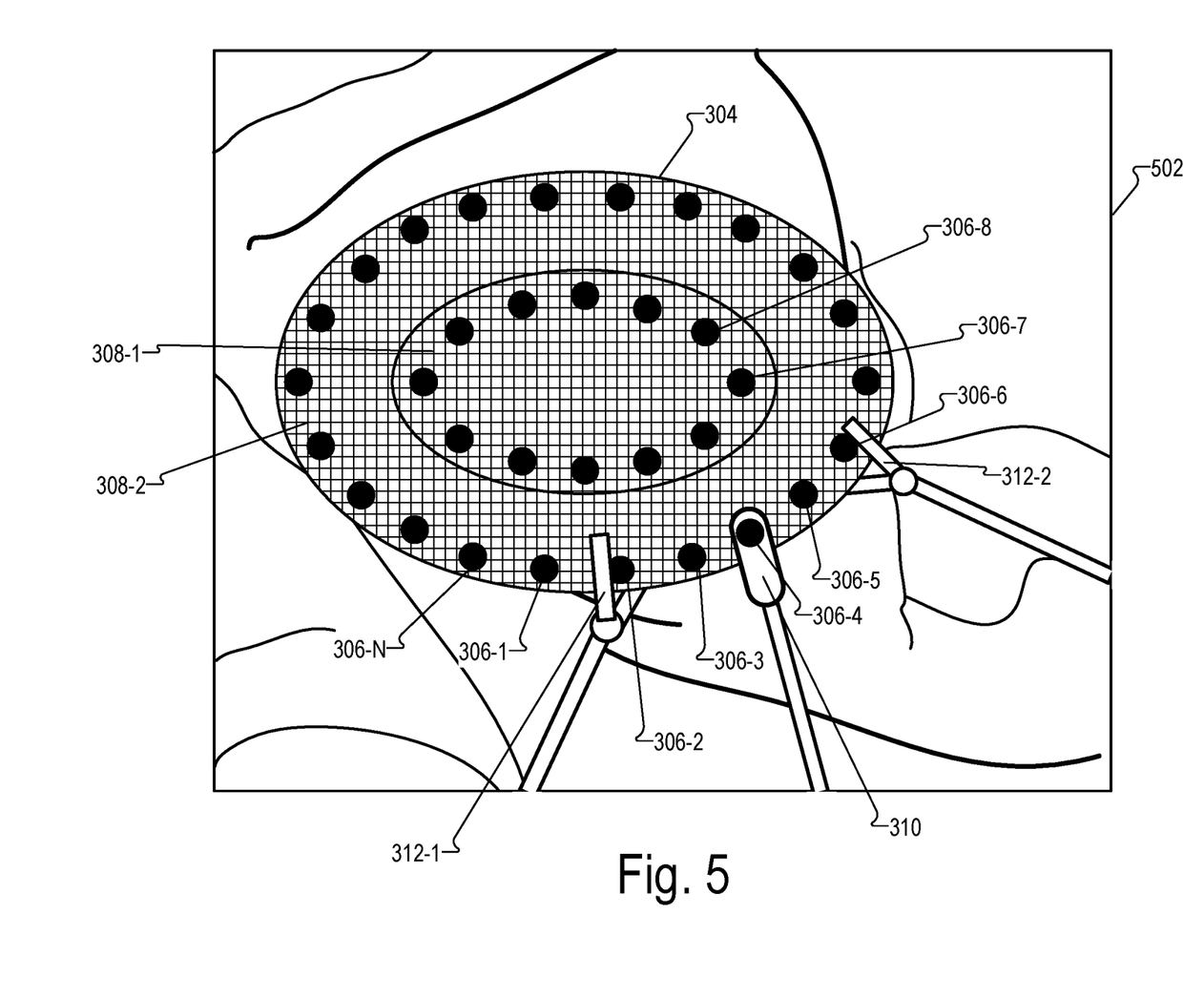
FIG. 5 shows an exemplary scenario in which a physical medical element is being placed on an anatomical surface according to principles described herein.

FIG. 5 shows an exemplary image 502 of the internal space shown in image 302, with physical medical element 304, suturing device 310, and surgical instruments 312. In image 502, system 100 has coordinated the movements of suturing device 310 and surgical instruments 312 to the next set of fiducial markers 306. Thus, surgical instrument 312-1 has been repositioned from fiducial marker 306-1 to a next fiducial marker to one side (e.g., a right side of fiducial marker 306-1), fiducial marker 306-2. Similarly, surgical instrument 312-2 has been repositioned from fiducial marker 306-5 to a next fiducial marker to the right, fiducial marker 306-6. Further, suturing device 310 has also been repositioned from fiducial marker 306-3 to a next fiducial marker over, fiducial marker 306-4. In this manner, system 100 may coordinate movements and repositioning of suturing device 310 to suture physical medical element 304 at each of target suture locations based on fiducial markers 306 while surgical instruments 312 hold physical medical element 304 in place. These coordinated movements may allow for system 100 to direct an automatic suturing of physical medical element 304 while avoiding collisions among suturing device 310 and surgical instruments 312.

While image 502 shows system 100 repositioning suturing device 310 and surgical instruments 312 to next fiducial markers to the right of initial fiducial markers in image 302, it should be evident that movements of suturing device 310 and surgical instruments 312 may be to a left of the initial fiducial markers or any other suitable direction. Additionally, while image 502 repositions each of suturing device 310 and surgical instruments 312 one fiducial marker over, any suitable number of fiducial markers may be used. Further, while images 302 and 502 show surgical instruments 312 each two fiducial markers away from suturing device 310, any suitable number of fiducial markers may be used. Additionally or alternatively, rather than or in conjunction with the fiducial markers, a specified distance from suturing device 310 may be used to guide movements of surgical instruments 312.

Furthermore, arm movement data 408 may be provided by system 100 based also on force sensing data 404. For instance, force sensing data 404 may indicate to system 100 that a collision has occurred among surgical instruments 312 and suturing device 310. In such an instance, system 100 may provide arm movement data 408 to move surgical instruments 312 away from suturing device 310 and/or each other. Additionally or alternatively, system 100 may adjust an operation of suturing device 310 based on the detecting of the collision. For example, system 100 may suspend an operation of suturing device 310 based on the detecting of the collision to ensure suturing device 310 does not suture an incorrect location due to movement caused by the collision.

As another example, surgical instruments 312 may provide force sensing data 404 to system 100 based on an amount of force generated on surgical instruments 312 by an anatomical surface. For example, an amount of force needed to hold physical medical element 304 against the anatomical surface may depend on a position, orientation, and/or contour of the anatomical surface and/or a relation of the anatomical surface to poses of surgical instruments 312 and suturing device 310. Thus, force sensing data 404 may be used to ensure that an appropriate amount of force is applied by surgical instruments 312 to keep physical medical element 304 in place while not damaging the anatomical surface. System 100 may determine the appropriate amount of force and include such determinations in arm movement data 408.

Figure 6:
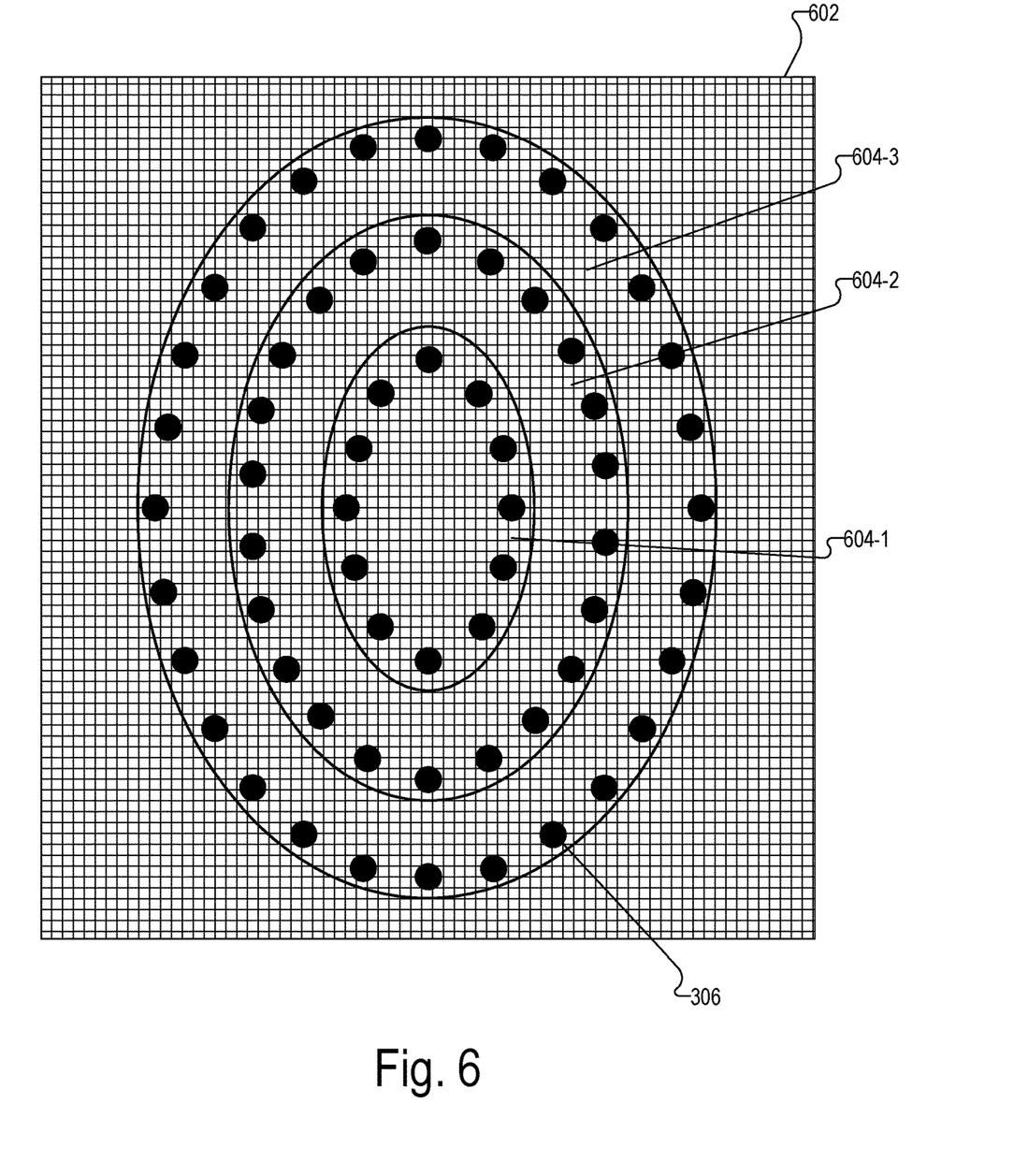
FIG. 6 shows an exemplary physical material from which a physical medical element is to be cut according to principles described herein.

FIG. 6 shows an exemplary physical material 602 from which a physical medical element (e.g., physical medical element 304) may be cut. Physical material 602 may be any suitable material, such as a mesh material from which patches for hernias and/or other types of tissue defects may be cut. As shown, physical material 602 may include concentric regions 604 (e.g., concentric region 604-1 through 604-3) of fiducial markers 306 pre-printed on physical material 602. Based on a size of a tissue defect on an anatomical surface, an appropriate size of the physical medical element may be determined. Based on the appropriate size, the physical medical element may be cut out of physical material 602. As concentric regions 604 of fiducial markers 306 are already pre-printed, the physical medical element may include concentric regions 604 of fiducial markers 306 that may be used by a medical element management system (e.g., system 100), for instance, to automatically suture the physical medical element to the anatomical surface as described herein.

Further, concentric regions 604 may be configured to be predetermined distances apart such that a dimension of the physical medical element may be identified by concentric regions 604. A user and/or system 100 may determine the appropriate size of physical medical element to be used for the size of tissue defect. Based on demarcations (e.g., lines) indicating concentric regions 604, a physical medical element of the appropriate size may be easily cut from physical material 602.

Additionally, physical material 602 may include a surface that is configured to self-adhere to an anatomical surface. The self-adhering surface may allow system 100 to suture a physical medical element cut from physical material 602 to the anatomical surface using fewer or no surgical instruments (e.g., surgical instruments 312) to hold the physical medical element to the anatomical surface.

Figure 7:
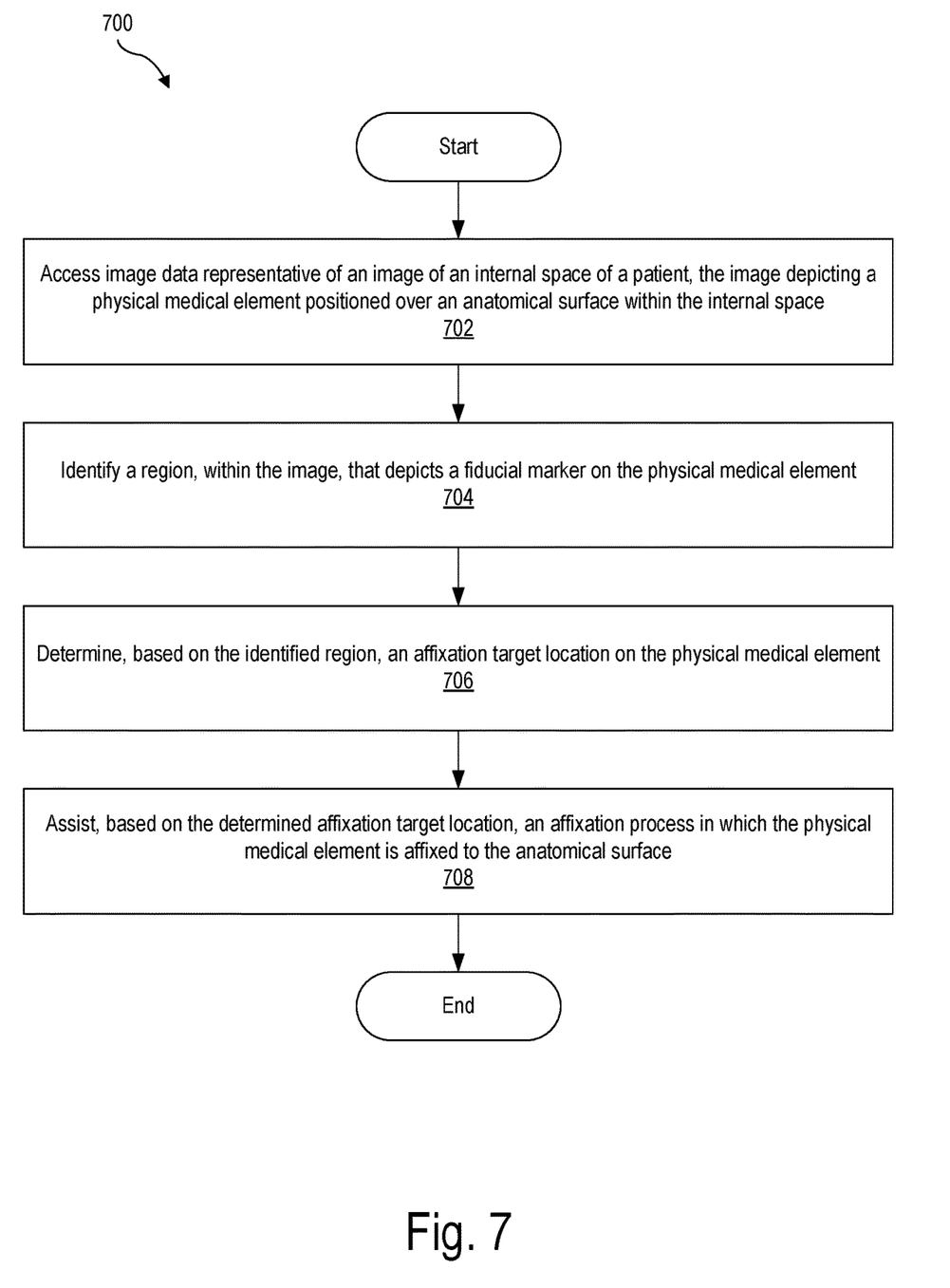
FIG. 7 illustrates an exemplary method according to principles described herein.

FIG. 7 illustrates an exemplary method 700 that may be performed by a medical element management system (e.g., system 100 and/or any implementation thereof). While FIG. 7 illustrates exemplary operations according to one embodiment, other embodiments may omit, add to, reorder, and/or modify any of the operations shown in FIG. 7.

In operation 702, a medical element management system accesses image data representative of an image of an internal space of a patient, the image depicting a physical medical element positioned over an anatomical surface within the internal space. Operation 702 may be performed in any of the ways described herein.

In operation 704, the medical element management system identifies a region, within the image, that depicts a fiducial marker on the physical medical element. Operation 704 may be performed in any of the ways described herein.

In operation 706, the medical element management system determines, based on the identified region, an affixation target location on the physical medical element. Operation 706 may be performed in any of the ways described herein.

In operation 708, the medical element management system assists, based on the determined affixation target location, an affixation process in which the physical medical element is affixed to the anatomical surface. Operation 708 may be performed in any of the ways described herein.

Figure 8:
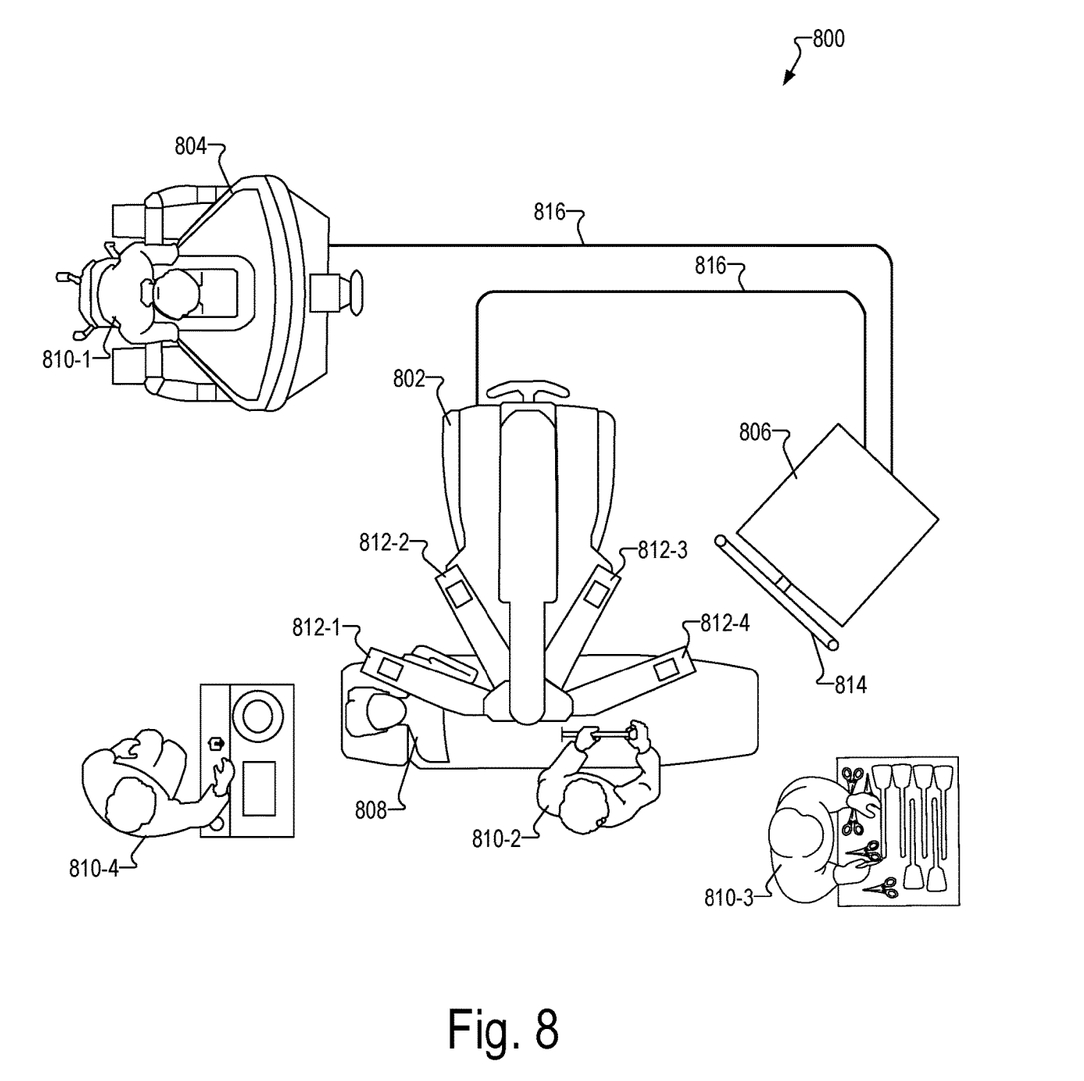
FIG. 8 illustrates an exemplary computer-assisted surgical system according to principles described herein.

The systems and methods described herein may be used in connection with and/or implemented by a computer-assisted surgical system used to perform a surgical procedure with respect to a patient. FIG. 8 illustrates an exemplary computer-assisted surgical system 800 ("surgical system 800"). As shown, surgical system 800 may include a manipulating system 802, a user control system 804, and an auxiliary system 806 communicatively coupled one to another. Surgical system 800 may be utilized by a surgical team to perform a computer-assisted surgical procedure on a patient 808. As shown, the surgical team may include a surgeon 810-1, an assistant 810-2, a nurse 810-3, and an anesthesiologist 810-4, all of whom may be collectively referred to as "surgical team members 810." Additional or alternative surgical team members may be present during a surgical session as may serve a particular implementation.

While FIG. 8 illustrates an ongoing minimally invasive surgical procedure, it will be understood that surgical system 800 may similarly be used to perform open surgical procedures or other types of surgical procedures that may similarly benefit from the accuracy and convenience of surgical system 800. Additionally, it will be understood that the surgical session throughout which surgical system 800 may be employed may not only include an operative phase of a surgical procedure, as is illustrated in FIG. 8, but may also include preoperative, postoperative, and/or other suitable phases of the surgical procedure. A surgical procedure may include any procedure in which manual and/or instrumental techniques are used on a patient to investigate or treat a physical condition of the patient.

As shown in FIG. 8, manipulating system 802 may include a plurality of manipulator arms 812 (e.g., manipulator arms 812-1 through 812-4) to which a plurality of surgical instruments may be coupled. Each surgical instrument may be implemented by any suitable therapeutic instrument (e.g., a tool having tissue-interaction functions), medical tool, imaging device (e.g., an endoscope), diagnostic instrument, or the like that may be used for a computer-assisted surgical procedure on patient 808 (e.g., by being at least partially inserted into patient 808 and manipulated to perform a computer-assisted surgical procedure on patient 808). In some examples, one or more of the surgical instruments may include force-sensing and/or other sensing capabilities. While manipulating system 802 is depicted and described herein as including four manipulator arms 812, it will be recognized that manipulating system 802 may include only a single manipulator arm 812 or any other number of manipulator arms as may serve a particular implementation.

Manipulator arms 812 and/or surgical instruments attached to manipulator arms 812 may include one or more displacement transducers, orientational sensors, and/or positional sensors used to generate raw (i.e., uncorrected) kinematics information. One or more components of surgical system 800 may be configured to use the kinematics information to track (e.g., determine positions of) and/or control the surgical instruments.

User control system 804 may be configured to facilitate control by surgeon 810-1 of manipulator arms 812 and surgical instruments attached to manipulator arms 812. For example, surgeon 810-1 may interact with user control system 804 to remotely move or manipulate manipulator arms 812 and the surgical instruments. To this end, user control system 804 may provide surgeon 810-1 with imagery (e.g., high-definition 3D imagery) of a surgical area associated with patient 808 as captured by an imaging system (e.g., any of the medical imaging systems described herein). In certain examples, user control system 804 may include a stereo viewer having two displays where stereoscopic images of a surgical area associated with patient 808 and generated by a stereoscopic imaging system may be viewed by surgeon 810-1. Surgeon 810-1 may utilize the imagery to perform one or more procedures with one or more surgical instruments attached to manipulator arms 812.

To facilitate control of surgical instruments, user control system 804 may include a set of master controls. These master controls may be manipulated by surgeon 810-1 to control movement of surgical instruments (e.g., by utilizing robotic and/or teleoperation technology). The master controls may be configured to detect a wide variety of hand, wrist, and finger movements by surgeon 810-1. In this manner, surgeon 810-1 may intuitively perform a procedure using one or more surgical instruments.

Auxiliary system 806 may include one or more computing devices configured to perform primary processing operations of surgical system 800. In such configurations, the one or more computing devices included in auxiliary system 806 may control and/or coordinate operations performed by various other components (e.g., manipulating system 802 and user control system 804) of surgical system 800. For example, a computing device included in user control system 804 may transmit instructions to manipulating system 802 by way of the one or more computing devices included in auxiliary system 806. As another example, auxiliary system 806 may receive, from manipulating system 802, and process image data representative of imagery captured by an imaging device attached to one of manipulator arms 812.

In some examples, auxiliary system 806 may be configured to present visual content to surgical team members 810 who may not have access to the images provided to surgeon 810-1 at user control system 804. To this end, auxiliary system 806 may include a display monitor 814 configured to display one or more user interfaces, such as images (e.g., 2D images, 3D images) of the surgical area, information associated with patient 808 and/or the surgical procedure, and/or any other visual content as may serve a particular implementation. For example, display monitor 814 may display images of the surgical area together with additional content (e.g., graphical content, contextual information, etc.) concurrently displayed with the images. In some embodiments, display monitor 814 is implemented by a touchscreen display with which surgical team members 810 may interact (e.g., by way of touch gestures) to provide user input to surgical system 800.

Manipulating system 802, user control system 804, and auxiliary system 806 may be communicatively coupled one to another in any suitable manner. For example, as shown in FIG. 8, manipulating system 802, user control system 804, and auxiliary system 806 may be communicatively coupled by way of control lines 816, which may represent any wired or wireless communication link as may serve a particular implementation. To this end, manipulating system 802, user control system 804, and auxiliary system 806 may each include one or more wired or wireless communication interfaces, such as one or more local area network interfaces, Wi-Fi network interfaces, cellular interfaces, etc.

In some examples, a non-transitory computer-readable medium storing computer-readable instructions may be provided in accordance with the principles described herein. The instructions, when executed by a processor of a computing device, may direct the processor and/or computing device to perform one or more operations, including one or more of the operations described herein. Such instructions may be stored and/or transmitted using any of a variety of known computer-readable media.

A non-transitory computer-readable medium as referred to herein may include any non-transitory storage medium that participates in providing data (e.g., instructions) that may be read and/or executed by a computing device (e.g., by a processor of a computing device). For example, a non-transitory computer-readable medium may include, but is not limited to, any combination of non-volatile storage media and/or volatile storage media. Exemplary non-volatile storage media include, but are not limited to, read-only memory, flash memory, a solid-state drive, a magnetic storage device (e.g. a hard disk, a floppy disk, magnetic tape, etc.), ferroelectric random-access memory ("RAM"), and an optical disc (e.g., a compact disc, a digital video disc, a Blu-ray disc, etc.). Exemplary volatile storage media include, but are not limited to, RAM (e.g., dynamic RAM).

Figure 9:
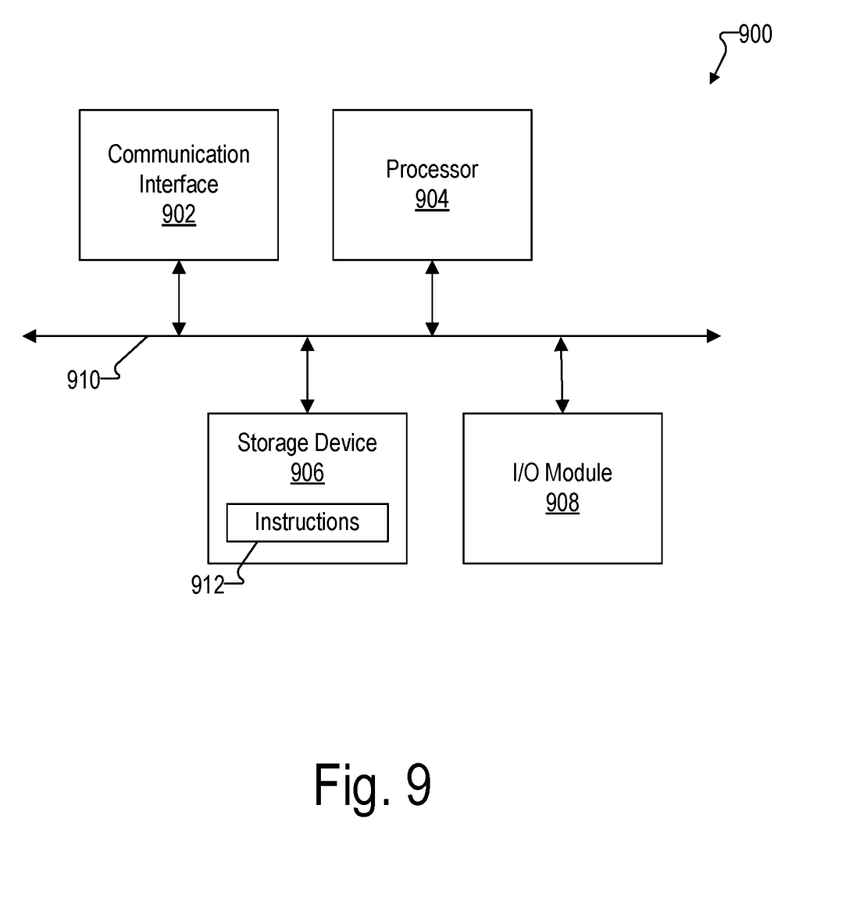
FIG. 9 illustrates an exemplary computing device according to principles described herein.

FIG. 9 illustrates an exemplary computing device 900 that may be specifically configured to perform one or more of the processes described herein. Any of the systems, computing devices, and/or other components described herein may be implemented by computing device 900.

As shown in FIG. 9, computing device 900 may include a communication interface 902, a processor 904, a storage device 906, and an input/output ("I/O") module 908 communicatively connected one to another via a communication infrastructure 910. While an exemplary computing device 900 is shown in FIG. 9, the components illustrated in FIG. 9 are not intended to be limiting. Additional or alternative components may be used in other embodiments. Components of computing device 900 shown in FIG. 9 will now be described in additional detail.

Communication interface 902 may be configured to communicate with one or more computing devices. Examples of communication interface 902 include, without limitation, a wired network interface (such as a network interface card), a wireless network interface (such as a wireless network interface card), a modem, an audio/video connection, and any other suitable interface.

Processor 904 generally represents any type or form of processing unit capable of processing data and/or interpreting, executing, and/or directing execution of one or more of the instructions, processes, and/or operations described herein. Processor 904 may perform operations by executing computer-executable instructions 912 (e.g., an application, software, code, and/or other executable data instance) stored in storage device 906.

Storage device 906 may include one or more data storage media, devices, or configurations and may employ any type, form, and combination of data storage media and/or device. For example, storage device 906 may include, but is not limited to, any combination of the non-volatile media and/or volatile media described herein. Electronic data, including data described herein, may be temporarily and/or permanently stored in storage device 906. For example, data representative of computer-executable instructions 912 configured to direct processor 904 to perform any of the operations described herein may be stored within storage device 906. In some examples, data may be arranged in one or more databases residing within storage device 906.

I/O module 908 may include one or more I/O modules configured to receive user input and provide user output. I/O module 908 may include any hardware, firmware, software, or combination thereof supportive of input and output capabilities. For example, I/O module 908 may include hardware and/or software for capturing user input, including, but not limited to, a keyboard or keypad, a touchscreen component (e.g., touchscreen display), a receiver (e.g., an RF or infrared receiver), motion sensors, and/or one or more input buttons.

I/O module 908 may include one or more devices for presenting output to a user, including, but not limited to, a graphics engine, a display (e.g., a display screen), one or more output drivers (e.g., display drivers), one or more audio speakers, and one or more audio drivers. In certain embodiments, I/O module 908 is configured to provide graphical data to a display for presentation to a user. The graphical data may be representative of one or more graphical user interfaces and/or any other graphical content as may serve a particular implementation.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A system comprising:
a memory storing instructions;
a processor communicatively coupled to the memory and configured to execute the instructions to:
   access image data representative of an image of an internal space of a patient, the image depicting a physical medical element positioned over an anatomical surface within the internal space;
   identify a region, within the image, that depicts a fiducial marker on the physical medical element;
   determine, based on the identified region, an affixation target location on the physical medical element; and
   direct, based on the determined affixation target location, an affixation process in which the physical medical element is affixed to the anatomical surface, wherein:
   the directing of the affixation process includes directing an affixation device coupled to a manipulator arm of a computer-assisted surgical system to affix the physical medical element to the anatomical surface at the affixation target location;
a surgical instrument coupled to an additional manipulator arm of the computer-assisted surgical system is configured to hold the physical medical element over the anatomical surface while the affixation device is used to affix the physical medical element to the anatomical surface; and
the processor is further configured to execute the instructions to:
   identify an additional region, within the image, that depicts an additional fiducial marker on the physical medical element;
   determine, based on the identified additional region, an additional affixation target location on the physical medical element;
   direct a movement of the affixation device from the affixation target to the additional affixation target location to affix the physical medical element to the anatomical surface at the additional affixation target location;
   direct a positioning of the surgical instrument at a first holding location on the physical medical element such that the affixation target location is between the first holding location and the additional affixation target location; and
   direct, in response to the movement of the affixation device from the affixation target location to the additional affixation target location, a repositioning of the surgical instrument to a second holding location on the physical medical element and that is closer to the additional affixation target location than the first holding location.

2. The system of claim 1, wherein:
the processor is further configured to execute the instructions to:
   direct a movement of at least one of the affixation device and the surgical instrument;
   obtain kinematic data associated with the movement; and
   perform, based on at least one of the kinematic data and the image data, a preventative measure configured to prevent at least one of a collision between the affixation device and the surgical instrument and a collision between the manipulator arm and the additional manipulator arm.

3. The system of claim 2, wherein the performing of the preventative measure comprises providing a warning.

4. The system of claim 3, wherein the warning comprises at least one of a visual alert, an audio alert, and a haptic alert.

5. The system of claim 2, wherein the performing of the preventative measure comprises automatically stopping the movement.

6. The system of claim 2, wherein the performing of the preventative measure comprises coordinating a movement of the affixation device and a movement of the surgical instrument in a manner that prevents a collision between the affixation device and the surgical instrument.

7. The system of claim 1, wherein a distance between the first affixation target location and the first holding location is substantially same as a distance between the second affixation target location and the second holding location.

8. The system of claim 1, wherein the first holding location corresponds to an additional fiducial marker on the physical medical element.

9. The system of claim 1, wherein
the processor is further configured to execute the instructions to:
   direct, subsequent to the affixing of the physical medical element to the anatomical surface at the first affixation target location, the repositioning of the surgical instrument from the first holding location to the second holding location that places the second affixation target location between the first affixation target location and the second holding location; and
   direct, subsequent to the repositioning of the surgical instrument, a repositioning of the affixation device to the second affixation target location.

10. The system of claim 1, wherein:
the first holding location is to a left of the affixation target location;
an additional surgical instrument coupled to an additional manipulator arm of the computer-assisted surgical system is configured to hold the physical medical element over the anatomical surface while the affixation device is used to affix the physical medical element to the anatomical surface; and
the processor is further configured to execute the instructions to:
   direct a positioning of the additional surgical instrument at a third holding location on the physical medical element such that the third holding location is to a right of the affixation target location;
   direct, subsequent to the directing of the affixation device to affix the physical medical element to the anatomical surface at the affixation target location, a repositioning of a closer to the additional affixation target location of the surgical instrument or the additional surgical instrument to a fourth holding location to a side of the additional affixation target location;
direct a repositioning of the affixation device to the additional affixation target location; and
direct a repositioning of a farther from the additional affixation target location of the surgical instrument or the additional surgical instrument to a fifth holding location to another side of the additional affixation target location.

11. The system of claim 10, wherein the first, second, third, and fourth holding locations each correspond to different fiducial markers on the physical medical element.

12. The system of claim 1, wherein
the processor is further configured to execute the instructions to:
direct a holding by the surgical instrument of the physical medical element against the anatomical surface;
obtain force sensing data representative of a force applied by the surgical instrument against the physical medical element while the surgical instrument holds the physical medical element against the anatomical surface;
determine, based on the force sensing data, that the surgical instrument is applying an amount of force outside a predetermined range; and
direct, based on the determining, a movement of the surgical instrument toward or away from the anatomical surface.

13. The system of claim 1, wherein
the processor is further configured to execute the instructions to:
direct a holding by the surgical instrument of the physical medical element over the anatomical surface;
direct a movement of the affixation device or the surgical instrument;
receive force sensing data associated with the movement from at least one of the affixation device and the surgical instrument;
detect, based on the force sensing data, at least one of a collision between the affixation device and the surgical instrument and a collision between the manipulator arm and the additional manipulator arm; and
suspend, in response to the detecting of the at least one of the collisions, an operation of the affixation device.

14. The system of claim 1, wherein:
the physical medical element comprises:
a plurality of concentric lines printed on a top surface of the physical medical element and that define a plurality of concentric regions on the physical medical element, and
a plurality of fiducial markers printed on the top surface within each of the concentric regions; and
the identifying of the plurality of regions that each depicts the fiducial marker on the physical medical element comprises:
identifying a concentric region that depicts an outermost concentric region of the plurality of concentric regions, the concentric region comprising the plurality of regions corresponding to a subset of fiducial markers in the plurality of fiducial markers.

15. A non-transitory computer-readable medium storing instructions that, when executed, direct at least one processor of a computing device to:
access image data representative of an image of an internal space of a patient, the image depicting a physical medical element positioned over an anatomical surface within the internal space;
identify a region, within the image, that depicts a fiducial marker on the physical medical element;
determine, based on the identified region, an affixation target location on the physical medical element; and
direct, based on the determined affixation target location, an affixation process in which the physical medical element is affixed to the anatomical surface, wherein:
the directing of the affixation process includes directing an affixation device coupled to a manipulator arm of a computer-assisted surgical system to affix the physical medical element to the anatomical surface at the affixation target location;
a surgical instrument coupled to an additional manipulator arm of the computer-assisted surgical system is configured to hold the physical medical element over the anatomical surface while the affixation device is used to affix the physical medical element to the anatomical surface; and
the processor is further configured to execute the instructions to:
identify an additional region, within the image, that depicts an additional fiducial marker on the physical medical element;
determine, based on the identified additional region, an additional affixation target location on the physical medical element;
direct a movement of the affixation device from the affixation target to the additional affixation target location to affix the physical medical element to the anatomical surface at the additional affixation target location;
direct a positioning of the surgical instrument at a first holding location on the physical medical element such that the affixation target location is between the first holding location and the additional affixation target location; and
direct, in response to the movement of the affixation device from the affixation target location to the additional affixation target location, a repositioning of the surgical instrument to a second holding location on the physical medical element and that is closer to the additional affixation target location than the first holding location.

16. A system comprising:
a memory storing instructions;
a processor communicatively coupled to the memory and configured to execute the instructions to:
access image data representative of an image of an internal space of a patient, the image depicting a physical medical element positioned over an anatomical surface within the internal space;
identify a region, within the image, that depicts a fiducial marker on the physical medical element;
determine, based on the identified region, an affixation target location on the physical medical element; and
direct, based on the determined affixation target location, an affixation process in which the physical medical element is affixed to the anatomical surface, wherein:
the directing of the affixation process includes directing an affixation device coupled to a manipulator arm of a computer-assisted surgical system to affix the physical medical element to the anatomical surface at the affixation target location;

a surgical instrument coupled to an additional manipulator arm of the computer-assisted surgical system is configured to hold the physical medical element over the anatomical surface for affixing the physical medical element while the affixation device is used to affix the physical medical element to the anatomical surface; and the processor is further configured to execute the instructions to:

direct a holding by the surgical instrument of the physical medical element against the anatomical surface;

obtain force sensing data representative of a force applied by the surgical instrument against the physical medical element while the surgical instrument holds the physical medical element against the anatomical surface;

determine, based on the force sensing data, that the surgical instrument is applying an amount of force outside a predetermined range; and direct, based on the determining that the surgical instrument is applying the amount of force outside the predetermined range, a movement of the surgical instrument toward or away from the anatomical surface.

17. The system of claim 16, wherein the processor is further configured to execute the instructions to:

direct a movement of at least one of the affixation device and the surgical instrument;

obtain kinematic data associated with the movement; and perform, based on at least one of the kinematic data and the image data, a preventative measure configured to prevent at least one of a collision between the affixation device and the surgical instrument and a collision between the manipulator arm and the additional manipulator arm.

18. The system of claim 17, wherein the performing of the preventative measure comprises providing a warning.

19. The system of claim 17, wherein the performing of the preventative measure comprises automatically stopping the movement.

20. The system of claim 17, wherein the performing of the preventative measure comprises coordinating a movement of the affixation device and a movement of the surgical instrument in a manner that prevents a collision between the affixation device and the surgical instrument.

* * * * *